(12) United States Patent
Inayama et al.

(10) Patent No.: US 8,772,531 B2
(45) Date of Patent: Jul. 8, 2014

US008772531B2

(54) NEOPENTYL GLYCOL DIESTER

(75) Inventors: Toshihiro Inayama, Mie (JP); Satoshi Hiyoshi, Mie (JP); Junya Kishi, Mie (JP); Masato Kujime, Mie (JP)

(73) Assignee: KH Neochem Co., Ltd., Tokyo (JP)

( * ) Notice: Subject to any disclaimer, the term of this patent is extended or adjusted under 35 U.S.C. 154(b) by 0 days.

(21) Appl. No.: 13/813,718

(22) PCT Filed: Jun. 30, 2011

(86) PCT No.: PCT/JP2011/065110
§ 371 (c)(1),
(2), (4) Date: Feb. 1, 2013

(87) PCT Pub. No.: WO2012/026215
PCT Pub. Date: Mar. 1, 2012

(65) Prior Publication Data
US 2013/0231498 A1    Sep. 5, 2013

(30) Foreign Application Priority Data
Aug. 24, 2010 (JP) .................................. 2010-187561

(51) Int. Cl.
*C07C 69/52* (2006.01)
(52) U.S. Cl.
USPC ....................................................... 560/190
(58) Field of Classification Search
CPC ...... C07C 57/13; C07C 51/353; C07C 67/08; C07C 59/28
See application file for complete search history.

(56) References Cited

U.S. PATENT DOCUMENTS

| | | | |
|---|---|---|---|
| 5,342,533 | A | 8/1994 | Kondo et al. |
| 5,395,544 | A | 3/1995 | Hagihara et al. |
| 5,653,909 | A | 8/1997 | Muraki et al. |
| 6,221,274 | B1 | 4/2001 | Akahori et al. |
| 6,228,820 | B1 | 5/2001 | Sakai et al. |

FOREIGN PATENT DOCUMENTS

| | | |
|---|---|---|
| CN | 1202880 A | 12/1998 |
| CN | 1097088 C | 12/2002 |
| JP | 6-17073 A | 1/1994 |
| JP | 6-25682 A | 2/1994 |
| JP | 6-108076 A | 4/1994 |
| WO | 97/11933 A1 | 4/1997 |
| WO | 2012/026303 | 3/2012 |

OTHER PUBLICATIONS

U.S. Appl. No. 13/813,695 to Toshihiro Inayama et al., which was filed Feb. 1, 2013.
U.S. Appl. No. 13/813,688 to Toshihiro Inayama et al., which was filed Feb. 1, 2013.
Taiwan Office action, mail date is Feb. 27, 2013.
Search report from International Application No. PCT/2011/065110, mail date is Aug. 9, 2011.
International Preliminary Report on Patentability No. PCT/JP2011/065110, mail date is Sep. 8, 2011.

*Primary Examiner* — Brandon Fetterolf
*Assistant Examiner* — Ana Z Muresan
(74) *Attorney, Agent, or Firm* — Greenblum & Bernstein, P.L.C.

(57) ABSTRACT

A neopentyl glycol diester which is a mixed ester of neopentyl glycol and carboxylic acids is provided, wherein the carboxylic acids consisting of isobutyric acid as well as 2-ethylhexanoic acid and/or 3,5,5-trimethylhexanoic acid. The neopentyl glycol diester may be used in a refrigerant oil or the like which exhibits excellent miscibility with a difluoromethane refrigerant among other properties.

7 Claims, No Drawings

NEOPENTYL GLYCOL DIESTER

TECHNICAL FIELD

The invention relates to a neopentyl glycol diester that may be used in an industrial lubricant (e.g., refrigerant oil) or the like.

BACKGROUND ART

In recent years, hydrofluorocarbons (HFC) that have zero ozone depletion potential (ODP) as well as a relatively low global warming potential (GWP) have been used as refrigerants for refrigerators. A difluoromethane refrigerant (HFC-32) has a low GWP that is about ⅓rd to ¼th of that of other refrigerants currently used (e.g., R-410A which is a mixture of difluoromethane and pentafluoroethane and R-407C which is a mixture of difluoromethane, pentafluoroethane and 1,1,1,2-tetrafluoroethane). Moreover, the difluoromethane refrigerant also has a coefficient of performance (COP) higher than that of R-410A, R-407C and the like by about 5 to 13% and therefore is a preferable refrigerant from the viewpoint of energy-saving (see Non-Patent Document 1).

Patent Document 1 discloses an ester of neopentyl glycol and 3,5,5-trimethylhexanoic acid that is used in a refrigerant oil for the difluoromethane refrigerant. However, the ester disclosed in Patent Document 1 is not satisfactory in that it does not exhibit sufficient miscibility with the difluoromethane refrigerant, for example.

RELATED-ART DOCUMENTS

Patent Document

Patent Document 1: JP H06-17073 A

Non-Patent Document

Non-Patent Document 1: Junkatsu Keizai, June 2004 (No. 460), p. 17

SUMMARY OF THE INVENTION

Technical Problem

An object of the present invention is to provide a neopentyl glycol diester that may be used in a refrigerant oil or the like that exhibits excellent miscibility with a difluoromethane refrigerant among other properties.

Solution to Problem

The invention provides the following neopentyl glycol diester.

[1] A neopentyl glycol diester that is a mixed ester of neopentyl glycol and carboxylic acids, the carboxylic acids comprising isobutyric acid as well as 2-ethylhexanoic acid and/or 3,5,5-trimethylhexanoic acid.

[2] The neopentyl glycol diester according to [1], wherein the molar ratio of isobutyric acid to 2-ethylhexanoic acid and/or 3,5,5-trimethylhexanoic acid (i.e., isobutyric acid/2-ethylhexanoic acid and/or 3,5,5-trimethylhexanoic acid ratio) in the carboxylic acids is 10/90 to 75/25.

[3] The neopentyl glycol diester according to [1] or [2], wherein the molar ratio of isobutyric acid to 2-ethylhexanoic acid and/or 3,5,5-trimethylhexanoic acid (i.e., isobutyric acid/2-ethylhexanoic acid and/or 3,5,5-trimethylhexanoic acid ratio) in the carboxylic acids is 26/74 to 75/25.

[4] The neopentyl glycol diester according to one of [1] to [3], wherein the carboxylic acids consist of isobutyric acid as well as 2-ethylhexanoic acid and/or 3,5,5-trimethylhexanoic acid.

Advantageous Effects of the Invention

The invention thus provides a neopentyl glycol diester that may be used in a refrigerant oil or the like exhibiting excellent miscibility with a difluoromethane refrigerant among other properties.

DESCRIPTION OF EMBODIMENTS

A neopentyl glycol diester (hereinafter may be referred to simply as "diester") according to the invention is a mixed ester of neopentyl glycol and carboxylic acids, the carboxylic acids comprising isobutyric acid as well as 2-ethylhexanoic acid and/or 3,5,5-trimethylhexanoic acid wherein the molar ratio of isobutyric acid to 2-ethylhexanoic acid and/or 3,5,5-trimethylhexanoic acid (i.e., isobutyric acid/2-ethylhexanoic acid and/or 3,5,5-trimethylhexanoic acid ratio) is preferably 10/90 to 75/25. More preferably, the molar ratio of isobutyric acid to 2-ethylhexanoic acid and/or 3,5,5-trimethylhexanoic acid in the carboxylic acids is 26/74 to 75/25.

The term "mixed ester" used herein includes (i) a neopentyl glycol diester in which the constituent carboxylic acids in one molecule consist of both isobutyric acid as well as 2-ethylhexanoic acid or 3,5,5-trimethylhexanoic acid; (ii) a mixture of a diester of neopentyl glycol and carboxylic acids comprising isobutyric acid, as well as a diester of neopentyl glycol and carboxylic acids comprising 2-ethylhexanoic acid, and/or a diester of neopentyl glycol and carboxylic acids comprising 3,5,5-trimethylhexanoic acid; and (iii) a mixture of (i) and (ii).

The neopentyl glycol diester according to the invention may comprise a neopentyl glycol monoester and the like as impurities.

When carboxylic acids which constitute the diester comprise isobutyric acid and 2-ethylhexanoic acid, the carboxylic acids may comprise other carboxylic acids in addition to isobutyric acid and 2-ethylhexanoic acid. Examples of the other carboxylic acids include linear aliphatic carboxylic acids (e.g., acetic acid, propionic acid, butyric acid, pentanoic acid, hexanoic acid, heptanoic acid, octanoic acid, nonanoic acid, decanoic acid, dodecanoic acid, tetradecanoic acid, hexadecanoic acid, and octadecanoic acid), branched aliphatic carboxylic acids (e.g., 2-methylbutyric acid, 3-methylbutyric acid, 2,2-dimethylpropanoic acid, 2-ethylbutyric acid, 2-methylpentanoic acid, 4-methylpentanoic acid, 2-methylhexanoic acid, 2-ethylpentanoic acid, 2-ethyl-2-methylbutyric acid, 2,2-dimethylpentanoic acid, 2-methylheptanoic acid, 3-ethylhexanoic acid, 2-ethyl-2-methylpentanoic acid, 3,5,5-trimethylhexanoic acid, 2-methyloctanoic acid, 2,2-dimethylheptanoic acid, isotridecanoic acid, and isostearic acid), and the like.

When carboxylic acids which constitute the diester comprise isobutyric acid and 3,5,5-trimethylhexanoic acid, the carboxylic acids may comprise other carboxylic acids in addition to isobutyric acid and 3,5,5-trimethylhexanoic acid. Examples of the other carboxylic acids include linear aliphatic carboxylic acids (e.g., acetic acid, propionic acid, butyric acid, pentanoic acid, hexanoic acid, heptanoic acid, octanoic acid, nonanoic acid, decanoic acid, dodecanoic acid, tetradecanoic acid, hexadecanoic acid, and octadecanoic acid), branched aliphatic carboxylic acids (e.g., 2-methylbutyric acid, 3-methylbutyric acid, 2,2-dimethylpropanoic acid, 2-ethylbutyric acid, 2-methylpentanoic acid, 4-methylpentanoic acid, 2-methylhexanoic acid, 2-ethylpentanoic acid, 2-ethyl-2-methylbutyric acid, 2,2-dimethylpentanoic acid, 2-methylheptanoic acid, 2-ethylhexanoic acid, 3-ethylhexanoic acid, 2-ethyl-2-methylpentanoic acid, 2-methyloctanoic acid, 2,2-dimethylheptanoic acid, isotridecanoic acid, and isostearic acid), and the like.

The content of the other carboxylic acids in the carboxylic acids comprising isobutyric acid as well as 2-ethylhexanoic acid and/or 3,3,5-trimethylhexanoic acid may be in a range without impairing excellent properties (e.g., miscibility with a difluoromethane refrigerant) of the neopentyl glycol diester. A molar ratio of the other carboxylic acids to the sum of isobutyric acid as well as 2-ethylhexanoic acid and/or 3,5,5-trimethylhexanoic acid (i.e., the other carboxylic acids/the sum of isobutyric acid as well as 2-ethylhexanoic acid and/or 3,5,5-trimethylhexanoic acid ratio) is preferably 0/100 to 5/100.

The carboxylic acids which constitute the neopentyl glycol diester preferably consist of isobutyric acid as well as 2-ethylhexanoic acid and/or 3,3,5-trimethylhexanoic acid.

The neopentyl glycol diester according to the invention may be produced, for example, by reacting neopentyl glycol and isobutyric acid as well as 2-ethylhexanoic acid and/or 3,5,5-trimethylhexanoic acid, and optionally the other carboxylic acids, at 120 to 250° C. for 5 to 60 hours, optionally in the presence of a catalyst.

Examples of the catalyst include mineral acids, organic acids, Lewis acids, organometals, solid acids, and the like. Specific examples of the mineral acids include hydrochloric acid, hydrofluoric acid, sulfuric acid, phosphoric acid, nitric acid, and the like. Specific examples of the organic acids include p-toluenesulfonic acid, benzenesulfonic acid, butanesulfonic acid, propanesulfonic acid, ethanesulfonic acid, methanesulfonic acid, and the like. Specific examples of the Lewis acids include boron trifluoride, aluminum chloride, tin tetrachloride, titanium tetrachloride, and the like. Specific examples of the organometals include tetrapropoxytitanium, tetrabutoxytitanium, tetrakis(2-ethylhexyloxy)titanium, and the like. Specific examples of the solid acids include a cation-exchange resin and the like.

The sum of the amount (mol) of isobutyric acid, the amount (mol) of 2-ethylhexanoic acid and/or 3,5,5-trimethylhexanoic acid and the amount (mol) of the other carboxylic acids is preferably larger than the amount (mol) of the hydroxyl groups of neopentyl glycol by a factor of 1.1 to 1.4.

In the reaction of neopentyl glycol and isobutyric acid as well as 2-ethylhexanoic acid and/or 3,5,5-trimethylhexanoic acid, and optionally the other carboxylic acids, a solvent may be used, examples of which include benzene, toluene and xylene.

It is preferable to carry out the reaction of neopentyl glycol and isobutyric acid as well as 2-ethylhexanoic acid and/or 3,5,5-trimethylhexanoic acid, and optionally the other carboxylic acids, while removing from the reaction mixture the water produced during the reaction. It should be noted that isobutyric acid may be incidentally removed from the reaction mixture when the water produced during the reaction is being removed.

After completion of the reaction, the resulting neopentyl glycol diester may optionally be purified by a method normally used in synthetic organic chemistry (e.g., washing with water and/or an alkaline aqueous solution, a treatment with activated carbon, an adsorbent, or the like, and various types of chromatography methods and distillation methods).

The neopentyl glycol diester according to the invention exhibits excellent miscibility with a difluoromethane refrigerant, excellent stability against oxidation, hydrolysis and heating, excellent low-temperature fluidity, and excellent lubricity, among other properties.

When the neopentyl glycol diester according to the invention is used in a refrigerant oil for a refrigerator, the kinematic viscosity of the neopentyl glycol diester at 40° C. is preferably 3 to 11 mm$^2$/sec, and the neopentyl glycol diester preferably has a two-phase separation temperature of −39° C. or lower. More preferably, the kinematic viscosity of the neopentyl glycol diester at 40° C. is 3 to 9 mm$^2$/sec, and the neopentyl glycol diester has a two-phase separation temperature of −43° C. or lower.

The neopentyl glycol diester according to the invention may be used in a refrigerant oil, as well as in an engine oil, a gear oil, grease, a plasticizer, and the like.

The refrigerant oil using the neopentyl glycol diester according to the invention may be a refrigerant oil comprising the neopentyl glycol diester of the invention and a lubricant additive, for example. In the refrigerant oil using the neopentyl glycol diester according to the invention, the neopentyl glycol diester is used as a lubricant base oil.

Examples of the lubricant additive include an antioxidant, a wear-reducing agent (e.g., anti-wear agent, anti-seize agent, and extreme pressure agent), a friction modifier, an acid scavenger, a metal deactivator, an anti-foaming agent, and the like which are usually used as lubricant additives. The amount of each additive in the refrigerant oil is preferably 0.001 to 5 wt %.

The neopentyl glycol diester according to the invention may be used in combination with other lubricant base oils. Examples of such additional lubricant base oils include a mineral oil, a synthetic base oil, and the like.

Examples of the mineral oil include paraffinic crude oils, intermediate base crude oils, naphthenic crude oils, and the like. A refined oil obtained by purifying any of said mineral oils via distillation or the like may also be used.

Examples of the synthetic base oil include poly-α-olefins (e.g., polybutene, polypropylene, and α-olefin oligomers having 8 to 14 carbon atoms), aliphatic esters other than the neopentyl glycol diester of the invention (e.g., fatty acid monoesters, fatty acid esters of a polyhydric alcohol, and aliphatic polybasic acid esters), aromatic esters (e.g., aromatic monoesters, aromatic esters of a polyhydric alcohol, and aromatic polybasic acid esters), polyalkylene glycols, polyvinyl ethers, polyphenyl ethers, alkylbenzenes, carbonates, synthetic naphthene, and the like.

EXAMPLES

The invention is further described below by providing Examples, Comparative Examples, and Test Examples. However, the invention is not limited to the examples.

The nuclear magnetic resonance spectrum [$^1$H-NMR, GSX-400 (400 MHz) manufactured by JEOL Ltd.; standard substance: tetramethylsilane; solvent: CDCl$_3$] of each of the neopentyl glycol diesters produced in Examples 1 to 9 and Comparative Example 1 was measured, and the molar ratio of isobutyric acid to 2-ethylhexanoic acid or the molar ratio of isobutyric acid to 3,5,5-trimethylhexanoic acid was calculated by the formula shown below.

Isobutyric acid/2-ethylhexanoic acid=integral value of peak $X$/integral value of peak $Y$ Isobutyric acid/3,5,5-trimethylhexanoic acid=integral value of peak $X$/integral value of peak $Z$ In the above formula, peak X corresponds to the peak of the hydrogen atom of the methine group of isobutyric acid, peak Y corresponds to the peak of the hydrogen atom of the methine group of 2-ethylhexanoic acid, and peak Z corresponds to the peak of the hydrogen atom of the methine group of 3,5,5-trimethylhexanoic acid.

Example 1

Production of Neopentyl Glycol Diester in which the Molar Ratio of Isobutyric Acid to 3,5,5-Trimethylhexanoic Acid (i.e., Isobutyric Acid/3,5,5-Trimethylhexanoic Acid Ratio) is 12/88 (Diester 1)

Kyowaad 500 manufactured by Kyowa Chemical Industry Co., Ltd. was used as an adsorbent.

Shirasagi P manufactured by Japan EnviroChemicals, Ltd. was used as activated carbon.

A reactor equipped with a Dean-Stark trap was charged with 417 g (4.0 mol) of neopentyl glycol (manufactured by Mitsubishi Gas Chemical Company, Inc.), 211 g (2.4 mol) of isobutyric acid (manufactured by Tokyo Chemical Industry Co., Ltd.), and 1139 g (7.2 mol) of 3,5,5-trimethylhexanoic acid (manufactured by Kyowa Hakko Chemical Co., Ltd.). The mixture was degassed by nitrogen bubbling at room temperature for 30 minutes with stirring.

The mixture was stirred at 150 to 220° C. for 12 hours while nitrogen bubbling was further continued. After the addition of 0.2 g of tetrabutoxytitanium, the reaction mixture was stirred at 220° C. for 3 hours. After completion of the reaction, the reaction mixture was stirred at 180° C. for 5 hours under a reduced pressure of 2.4 kPa to remove unreacted carboxylic acids from the reaction product by distillation. The reaction product was washed at 80° C. for 1 hour with 500 mL of an alkaline aqueous solution containing sodium hydroxide at 2-fold molar excess relative to the acid number of the reaction product. The reaction product was then washed with 500 mL of water at 80° C. for 30 minutes (three times). Next, the reaction product was stirred at 90° C. for 1 hour under a reduced pressure of 1.3 kPa with nitrogen bubbling to dry the reaction product.

After the addition of 10 g of the adsorbent (corresponding to 1 wt % of the reaction product) and 10 g of activated carbon (corresponding to 1 wt % of the reaction product), the mixture was stirred at 90° C. for 1 hour under a reduced pressure of 1.3 kPa with nitrogen bubbling, and then filtered by using a filter aid, to finally obtain 1091 g of Diester 1.

Example 2

Production of Neopentyl Glycol Diester in which the Molar Ratio of Isobutyric Acid to 3,5,5-Trimethylhexanoic Acid (i.e., Isobutyric Acid/3,5,5-Trimethylhexanoic Acid Ratio) is 17/83 (Diester 2)

Diester 2 was obtained in the same manner as in Example 1, except that the molar ratio of neopentyl glycol, isobutyric acid and 3,5,5-trimethylhexanoic acid (i.e., neopentyl glycol/isobutyric acid/3,5,5-trimethylhexanoic acid ratio) was changed to 1/0.72/1.68.

Example 3

Production of Neopentyl Glycol Diester in which the Molar Ratio of Isobutyric Acid to 3,5,5-Trimethylhexanoic Acid (i.e., Isobutyric acid/3,5,5-Trimethylhexanoic Acid Ratio) is 23/77 (Diester 3)

Diester 3 was obtained in the same manner as in Example 1, except that the molar ratio of neopentyl glycol, isobutyric acid and 3,5,5-trimethylhexanoic acid (i.e., neopentyl glycol/isobutyric acid/3,5,5-trimethylhexanoic acid ratio) was changed to 1/0.84/1.56.

Example 4

Production of Neopentyl Glycol Diester in which the Molar Ratio of Isobutyric Acid to 3,5,5-Trimethylhexanoic Acid (i.e., Isobutyric acid/3,5,5-Trimethylhexanoic Acid Ratio) is 26/74 (Diester 4)

Diester 4 was obtained in the same manner as in Example 1, except that the molar ratio of neopentyl glycol, isobutyric acid and 3,5,5-trimethylhexanoic acid (i.e., neopentyl glycol/isobutyric acid/3,5,5-trimethylhexanoic acid ratio) was changed to 1/0.96/1.44.

Example 5

Production of Neopentyl Glycol Diester in which the Molar Ratio of Isobutyric Acid to 3,5,5-Trimethylhexanoic Acid (i.e., Isobutyric Acid/3,5,5-Trimethylhexanoic Acid Ratio) is 38/62 (Diester 5)

Diester 5 was obtained in the same manner as in Example 1, except that the molar ratio of neopentyl glycol, isobutyric acid and 3,5,5-trimethylhexanoic acid (i.e., neopentyl glycol/isobutyric acid/3,5,5-trimethylhexanoic acid ratio) was changed to 1/1.20/1.20.

Example 6

Roduction of Neopentyl Glycol Diester in which the Molar Ratio of Isobutyric Acid to 3,5,5-Trimethylhexanoic Acid (i.e., Isobutyric Acid/3,5,5-Trimethylhexanoic Acid Ratio) is 74/26 (Diester 6)

Diester 6 was obtained in the same manner as in Example 1, except that the molar ratio of neopentyl glycol, isobutyric acid and 3,5,5-trimethylhexanoic acid (i.e., neopentyl glycol/isobutyric acid/3,5,5-trimethylhexanoic acid ratio) was changed to 1/2.16/0.24.

Example 7

Production of Neopentyl Glycol Diester in which the Molar Ratio of Isobutyric Acid to 2-Ethylhexanoic Acid (i.e., Isobutyric Acid/2-Ethylhexanoic Acid Ratio) is 27/73 (Diester 7)

Diester 7 was obtained in the same manner as in Example 1, except that 2-ethylhexanoic acid (manufactured by Kyowa Hakko Chemical Co., Ltd.) was used instead of 3,5,5-trimethylhexanoic acid, and neopentyl glycol, isobutyric acid and 2-ethylhexanoic acid were used in a molar ratio (i.e., neopentyl glycol/isobutyric acid/2-ethylhexanoic acid ratio) of 1/0.72/1.68.

Example 8

Production of Neopentyl Glycol Diester in which the Molar Ratio of Isobutyric Acid to 2-Ethylhexanoic Acid (i.e., Isobutyric Acid/2-Ethylhexanoic Acid Ratio) is 46/54 (Diester 8)

Diester 8 was obtained in the same manner as in Example 1, except that 2-ethylhexanoic acid (manufactured by Kyowa Hakko Chemical Co., Ltd.) was used instead of 3,5,5-trimethylhexanoic acid, and neopentyl glycol, isobutyric acid and 2-ethylhexanoic acid were used in a molar ratio (i.e., neopentyl glycol/isobutyric acid/2-ethylhexanoic acid ratio) of 1/1.20/1.20.

Example 9

Production of Neopentyl Glycol Diester in which the Molar Ratio of Isobutyric Acid to 2-Ethylhexanoic Acid (i.e., Isobutyric Acid/2-Ethylhexanoic Acid Ratio) is 72/28 (Diester 9)

Diester 9 was obtained in the same manner as in Example 1, except that 2-ethylhexanoic acid (manufactured by Kyowa Hakko Chemical Co., Ltd.) was used instead of 3,5,5-trimethylhexanoic acid, and neopentyl glycol, isobutyric acid and 2-ethylhexanoic acid were used in a molar ratio (i.e., neopentyl glycol/isobutyric acid/2-ethylhexanoic acid ratio) of 1/1.92/0.48.

Comparative Example 1

Production of Diester of Neopentyl Glycol and 3,5,5-Trimethylhexanoic Acid (Diester A)

Diester A was obtained in the same manner as in Example 1, except that the molar ratio of neopentyl glycol, isobutyric acid and 3,5,5-trimethylhexanoic acid (i.e., neopentyl glycol/isobutyric acid/3,5,5-trimethylhexanoic acid ratio) was changed to 1/0/2.4.

Test Example 1

Measurement of Kinematic Viscosity

Kinematic viscosity of each of Diesters 1 to 9 and A at 40° C. was measured in accordance with JIS K2283:2000 by using a Cannon-Fenske viscometer. The results are shown in Tables 1 and 2.

Test Example 2

Measurement of Two-Phase Separation Temperature

The two-phase separation temperatures of Diesters 1 to 9 and A were measured in accordance with JIS K2211:2009. Specifically, a pressure-resistant glass tube was charged with 0.4 g of the diester (Diester 1 to 9 or A) and 3.6 g of a difluoromethane refrigerant, and each of the mixtures was cooled from 30° C. at a rate of 0.5° C./min. The temperature at which the mixture was separated into two phases or became cloudy was defined as the two-phase separation temperature. The results are shown in Tables 1 and 2.

TABLE 1

| Diester | Isobutyric acid/ 3,5,5-trimethylhexanoic acid ratio (molar ratio) | Kinematic viscosity ($mm^2$/sec) | Two-phase separation temp. (° C.) |
|---|---|---|---|
| A(Comp. Example 1) | 0/100 | 13.0 | −32 |
| 1(Example 1) | 12/88 | 10.7 | −39 |
| 2(Example 2) | 17/83 | 10.0 | −42 |
| 3(Example 3) | 23/77 | 9.1 | −46 |
| 4(Example 4) | 26/74 | 8.6 | −48 |
| 5(Example 5) | 38/62 | 7.1 | ≤−50 |
| 6(Example 6) | 74/26 | 3.9 | ≤−50 |

TABLE 2

| Diester | Isobutyric acid/ 2-ethylhexanoic acid ratio (molar ratio) | Kinematic viscosity ($mm^2$/sec) | Two-phase separation temp. (° C.) |
|---|---|---|---|
| 7(Example 7) | 27/73 | 5.7 | −43 |
| 8(Example 8) | 46/54 | 4.6 | ≤−50 |
| 9(Example 9) | 72/28 | 3.4 | ≤−50 |

As shown in Table 1, Diesters 1 to 6 had a kinematic viscosity at 40° C. of 3.9 to 10.7 $mm^2$/sec and had a two-phase separation temperature of −39° C. or lower, indicating excellent miscibility with the difluoromethane refrigerant. Among them, Diesters 4 to 6 had a kinematic viscosity at 40° C. of 3.9 to 8.6 $mm^2$/sec and had a two-phase separation temperature of −48° C. or lower, indicating especially excellent miscibility with the difluoromethane refrigerant.

As shown in Table 2, Diesters 7 to 9 had a kinematic viscosity at 40° C. of 3.4 to 5.7 $mm^2$/sec and had a two-phase separation temperature of −43° C. or lower, indicating excellent miscibility with the difluoromethane refrigerant.

Test Example 3

Rotaring Bomb Oxidation Stability Test

Oxidation stability of Diester 6 was measured in accordance with JIS K2514-1996 by using a rotating bomb oxidation tester (RBOT-02; manufactured by Rigo Co., LTD.).

Specifically, a pressure vessel was charged with 49.75 g of Diester 6, 0.25 g of 4,4'-methylenebis(2,6-di-tert-butylphenol), 5 mL of water, and electrolytic copper wire (diameter: 1.6 mm; length: 3 m) polished with sandpaper. The pressure vessel was pressurized to 620 kPa by oxygen, after which the vessel was placed in a thermostatic bath at 150° C., and was then rotated at 100 rpm. The time required to achieve a pressure drop of 175 kPa after a pressure of the pressure vessel reached maximum was 118 minutes for Diester 6. The result indicates that Diester 6 has excellent stability against oxidation.

INDUSTRIAL APPLICABILITY

The present invention thus provides a neopentyl glycol diester that may be used in a refrigerant oil or the like which exhibits excellent miscibility with a difluoromethane refrigerant among other properties.

The invention claimed is:

1. A neopentyl glycol diester that is a mixed ester of neopentyl glycol and carboxylic acids, the carboxylic acids consisting of isobutyric acid, as well as 2-ethylhexanoic acid and/or 3,5,5-trimethylhexanoic acid.

2. The neopentyl glycol diester according to claim 1, wherein the molar ratio of isobutyric acid to 2-ethylhexanoic acid and/or 3,5,5-trimethylhexanoic acid (isobutyric acid/2-ethylhexanoic acid and/or 3,5,5-trimethylhexanoic acid ratio) in the carboxylic acids is 10/90 to 75/25.

3. The neopentyl glycol diester according to claim 1, wherein the molar ratio of isobutyric acid to 2-ethylhexanoic acid and/or 3,5,5-trimethylhexanoic acid (isobutyric acid/2-ethylhexanoic acid and/or 3,5,5-trimethylhexanoic acid ratio) in the carboxylic acids is 26/74 to 75/25.

4. The neopentyl glycol diester according to claim 2, wherein the molar ratio of isobutyric acid to 2-ethylhexanoic acid and/or 3,5,5-trimethylhexanoic acid (isobutyric acid/2-ethylhexanoic acid and/or 3,5,5-trimethylhexanoic acid ratio) in the carboxylic acids is 26/74 to 75/25.

5. The neopentyl glycol diester according to claim 2, wherein the carboxylic acids consist of isobutyric acid as well as 2-ethylhexanoic acid and/or 3,5,5-trimethylhexanoic acid.

6. The neopentyl glycol diester according to claim 3, wherein the carboxylic acids consist of isobutyric acid as well as 2-ethylhexanoic acid and/or 3,5,5-trimethylhexanoic acid.

7. The neopentyl glycol diester according to claim 4, wherein the carboxylic acids consist of isobutyric acid as well as 2-ethylhexanoic acid and/or 3,5,5-trimethylhexanoic acid.

\* \* \* \* \*